(12) United States Patent
Habrich et al.

(10) Patent No.: US 12,243,639 B2
(45) Date of Patent: Mar. 4, 2025

(54) LIQUID HANDLING IN AUTOMATED ANALYSER SYSTEMS

(71) Applicant: STRATEC SE, Birkenfeld (DE)

(72) Inventors: Thilo Habrich, Bad Wildbad (DE); Harald Tahedl, Wimsheim (DE); Tobias Wienhold, Karlsruhe (DE)

(73) Assignee: STRATEC SE, Birkenfeld (DE)

( * ) Notice: Subject to any disclaimer, the term of this patent is extended or adjusted under 35 U.S.C. 154(b) by 417 days.

(21) Appl. No.: 17/698,232

(22) Filed: Mar. 18, 2022

(65) Prior Publication Data

US 2022/0301703 A1  Sep. 22, 2022

(30) Foreign Application Priority Data

Mar. 18, 2021 (EP) .................................. 21163409

(51) Int. Cl.
*G16H 40/40* (2018.01)
*G01N 35/00* (2006.01)
*G01N 35/10* (2006.01)

(52) U.S. Cl.
CPC .......... *G16H 40/40* (2018.01); *G01N 35/1016* (2013.01); *G01N 35/00594* (2013.01); *G01N 2035/1018* (2013.01)

(58) Field of Classification Search
None
See application file for complete search history.

(56) References Cited

U.S. PATENT DOCUMENTS

| | | | |
|---|---|---|---|
| 5,777,221 A | 7/1998 | Murthy et al. | |
| 5,940,290 A | 8/1999 | Dixon | |
| 2007/0059184 A1 | 3/2007 | Bach | |
| 2010/0102974 A1* | 4/2010 | Keast | F15B 19/005 340/626 |
| 2012/0096940 A1* | 4/2012 | Burkart | G01N 35/1009 73/295 |
| 2014/0010675 A1* | 1/2014 | Kent | F04B 43/009 417/476 |
| 2019/0304600 A1 | 10/2019 | Mogatadakala | |
| 2020/0013501 A1 | 1/2020 | Page et al. | |

FOREIGN PATENT DOCUMENTS

KR  102019126596 A1  11/2019

* cited by examiner

*Primary Examiner* — Raymond L Nimox
(74) *Attorney, Agent, or Firm* — 24IP Law Group USA, PLLC; Timothy R DeWitt

(57) ABSTRACT

A method for determining the quality of a hose in an automated analyser system, comprising the steps of collecting data of a wash curve by measuring the light intensity through a hose with an optical sensor during washing of a hose; determining and recording the voltage changes related to changing light intensities; extracting an aspiration time and time for completing of a an aspiration process from said data; determining changes in the data of the most recent wash curves. The disclosure further relates to a device for preforming said method.

12 Claims, 1 Drawing Sheet

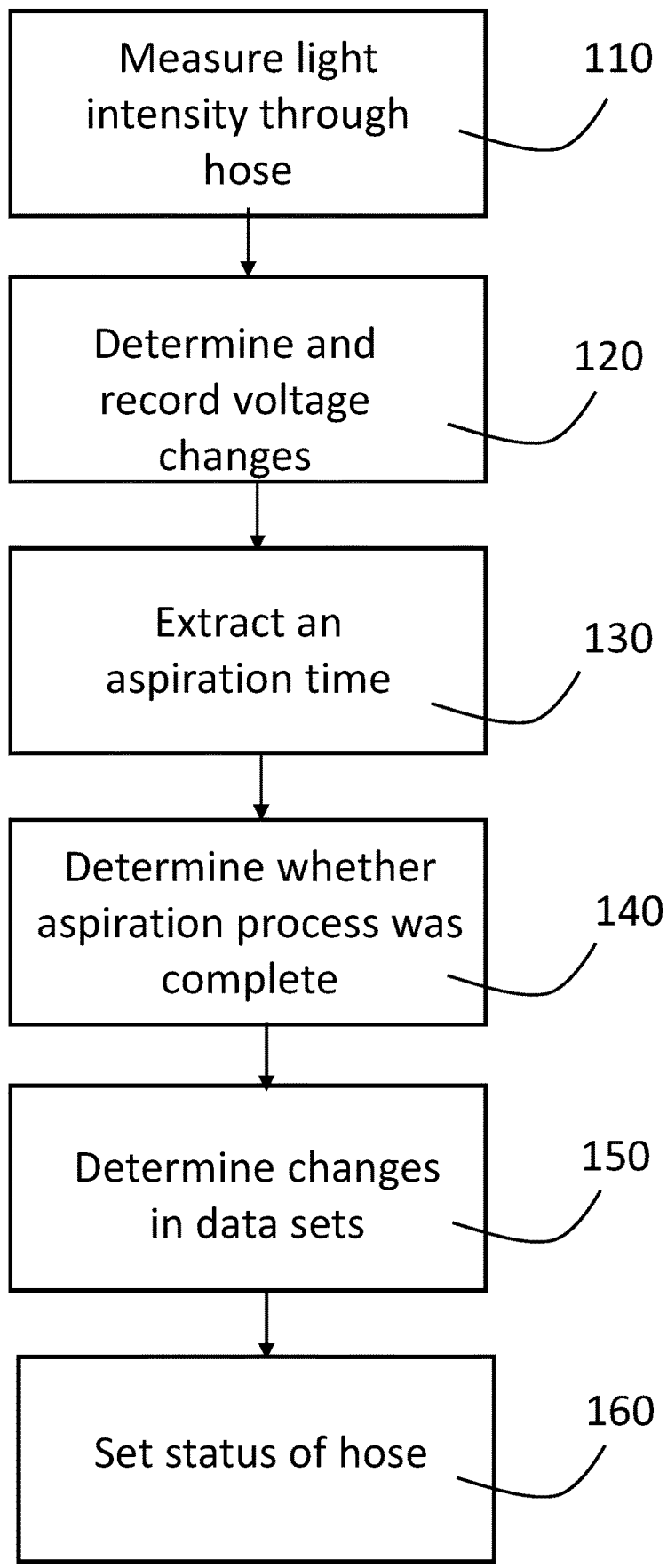

LIQUID HANDLING IN AUTOMATED ANALYSER SYSTEMS

CROSS-REFERENCE TO RELATED APPLICATIONS

The present invention claims priority to European patent application no. EP 21 163 409.2 filed on Mar. 18, 2021. The afore mentioned application is incorporated herein by reference.

BACKGROUND OF THE INVENTION

Field of the Invention

The invention relates to a method and a device for determining the quality of a hose in an automated analyser system.

Brief Description of the Related Art

Automated analyser systems for use in clinical diagnostics and life sciences are produced by a number of companies. For example, STRATEC® SE, Birkenfeld, Germany, produces a number of devices for specimen handling and detection for use in automated analyser systems and other laboratory instrumentation.

Complex medical devices like in vitro diagnostic (IVD) devices for processing diagnostic assays, can be formed by a large number of individual device components, hereinafter referred to as modules. These modules take over individual processing steps in the sample processing sequence. The functionality required for these processing steps is provided by the firmware of the modules. As a rule, data is collected during processing and checked by means of a process control. These process controls are used to analyse the collected parameters and to ensure a correct analysis procedure. If abnormal behaviour is detected during the process control, the currently processed sample is discarded if necessary.

A central task of these IVD devices is the movement of liquids. A correct and complete movement, such as aspiration, of the fluids is essential for the correct functionality of the devices. The aspiration of fluid is performed by a peristaltic pump. A peristaltic pump is based on the reshaping and pressing of tubes for transporting liquids. Due to this constant reshaping, mechanical wear occurs on the hoses after a certain period of use. Due to the mechanical wear, the pumping process can be impaired as the hoses age, which can be detected by the process control system. As a result, the process control initiates a repetition of the running process or may initiate a complete termination of the process.

Published U.S. Pat. No. 5,940,290 relates to a pipeline system of a process facility has a plurality of equipment, the equipment including at least one pipeline for providing a channel for a fluid of a process to flow. The process of the process facility is controlled by a process control system. The equipment also includes at least one device for measuring a process variable of the fluid. The device comprises a sensor element for sensing a predetermined process variable of the fluid flowing in the pipeline to output a signal containing information about the process variable being measured and containing information about the fluid flowing in the pipeline. The device further includes a first filter to pass a first component of the signal containing the information of the process variable and a second filter to pass a second component of the signal containing the information about the fluid flowing in the pipeline. A first processor processes the first component of the signal to output the process variable to the process control system to control the process. A second processor processes the second component of the signal in a flow model of the pipeline system to output advisory information indicating imminent failure of the equipment when detected by said processing by the second processor.

Published Korean Patent Application No. KR 102019126596 A relates to a monitoring system for predictive maintenance of a sewage pump and, more specifically, to a monitoring system for predictive maintenance of a sewage pump, which can rapidly predict and determine whether a sewage pump has defects. To achieve this, a monitoring system for predictive maintenance of a pump comprises a sensor unit installed in the pump and measuring vibration, temperature, and currents of a bearing and a pollution level of mechanical seal oil to acquire sensing information. The sensing information measured by the sensor unit is analysed to monitor whether the sewage pump has defects.

Published U.S. Patent Application No. US 2020/0013501 A1 relates to systems and methods for managing the maintenance for a plurality of monitored medical devices and includes to receive streaming time series medical device data from the plurality of monitored medical devices. The streaming time series medical device data is analysed to determine an operational status of a component of a medical device of the plurality of monitored medical devices. A maintenance procedure for the medical device is determined from the operational status of the component of the medical device.

Published U.S. Patent Application No. US 2019/0304600 A1 provides components, systems, and methods for predictive maintenance of medical diagnostic machine components.

Disadvantages of the available solutions refer to the fact there is no indication of the current condition of the hoses so that the hoses are replaced at set intervals. This sometimes leads to good hoses being replaced. In addition, hoses may fail before the end of the replacement interval. This leads to the accumulation of abnormal behaviour detection by the process control and ultimately to the temporary failure of the unit until the hoses are replaced.

SUMMARY OF THE INVENTION

It is therefore the object of this invention to provide a device and a method for predicting or detecting the wear or failure of a hose in an automated analyser system.

The present invention provides a method for determining the quality of a hose in a peristaltic pump of an automated analyser system, comprising the steps of:
  collecting data of an aspiration process through the hose by:
    i. measuring the light intensity through the hose during aspiration with an optical sensor; and
    ii. determining and recording the voltage changes related to changing light intensities measured by the optical sensor;
  extracting an aspiration time and determining whether the aspiration process was completed from two sets of data of voltage changes relating to the aspiration time and whether the aspiration process was completed; and determining changes in the two sets of data of voltage changes for the aspiration time and the determination whether the process was completed.

The method refers in a further aspect to a threshold that is set for each set of data of voltage changes for the aspiration time and the time for completing the aspiration process for indicating wear of the hose when at least one of the thresholds is exceeded or not reached, respectively.

The state of the hose is classified as normal if none of both thresholds is exceeded or not reached, respectively, in a further embodiment of the method according to the present invention.

It may also be intended that the state of the hose is set to 'warning' if at least one threshold is exceeded or not reached, respectively.

The method refers in another aspect to the state of the hose that is set to 'critical' if both thresholds are exceeded or not reached, respectively.

It is envisaged that the remaining useful lifetime of the hose is determined in days based on the average use of the automated analyser system per day.

The method may further encompass that the state of the hose is set to 'total failure' when the last day of the determined days of the remaining useful lifetime has been reached.

In another embodiment of a method according to the present disclosure, the state of the hose is set back to 'normal' following its replacement and the detection that none of both thresholds is exceeded or not reached, respectively.

The method may further refer to the recent 40 wash curves which are used for determining changes in the two sets of data of voltage changes for the aspiration time and for determining whether the aspiration process was completed.

Another aspect of the method according to the present disclosure refers to the recording of voltages of a light barrier's photodiode is done at high frequencies during a washing process.

Another object of the present invention relates to the use of a method according to any one of claims 1 to 10 for determining the quality of a hose in a peristaltic pump of an automated analyser system.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE FIGURES

For a more complete understanding of the present invention and the advantages thereof, reference is now made to the following description and the accompanying drawings, in which:

FIG. 1 is a flow chart illustrating a preferred embodiment of a method in accordance with the present invention.

DETAILED DESCRIPTION OF THE INVENTION

The technical problem is solved by the independent claims. The dependent claims cover further specific embodiments of the invention.

Unplanned maintenance cause extensions of the sample analysis or costly downtimes of the instrument. The device and method of the present invention is intended to predict and/or detect mechanical wear applied to parts of a peristaltic pump so that problems related to the mechanical wear can be predicted ahead of time. The replacement of relevant components can be planned at favourable times using said information.

The device of the present invention can be used to perform a method for predicting or determining at what time point a hose will cause a high number of measurement repetitions. For this purpose, the method provides a continuous assessment of all hoses and points to problems which may occur in the future. In addition, at the end of the service life, an estimate is made of the remaining service life.

One important component in a device according to the present invention is the washing stations for rinsing the samples before measurement. So-called bubble sensors, which can distinguish between air and liquid in the tubing, have so far only been used for carrying out process control, i.e., a qualitative analysis of individual aspirations by measuring the aspiration times. Permanent monitoring of the condition of peristaltic tubes, based on continuous measurements of suction times, has not been possible so far.

A first bubble sensor variant is based on the transmitted light principle. The sensors consist of a sensor body (injection moulding), a hinged cover with snap-in hook (injection moulding) and a forked light barrier mounted on a printed circuit board (PCB). The hose or tube is inserted between light source and optical sensor of the light barrier. The cover, which closes via snap-in hooks, holds the tube in position. The measured optical signal differs depending on whether the hose or tube is filled with liquid or with air.

A further bubble sensor variant is based on the principle of total reflection. The sensor comprises a polymer or silicone (injection moulding) housing which is pushed over the hose to be monitored. The transmitter and receiver of a light barrier are located in this housing and are arranged at an angle <180° with respect to each other, as the measurement is not based on the transmitted light principle, i.e., attenuation measurement, but on the total reflection principle. In the case of an air-filled hose, almost all the light is reflected at the inner wall of the hose and directed to the receiver. The angle at which the transmitter, receiver and hose are arranged in relation to each other must be adjusted so that total reflection is possible. In the case of a liquid-filled hose, the emitted light can enter the liquid through the hose's walls, i.e., it is not reflected, so the measured signal differs significantly from the signal of an air-filled hose.

A first aspect of the present disclosure relates to a light barrier sensor that allows continuous measurements of suction times of liquids to be collected. The invention relates further to a method that evaluates the continuously measured aspiration times and determines an estimate of the quality of the hoses used for aspiration. Furthermore, the method allows a prediction of the remaining useful lifetime of the hoses (Remaining Useful Life). The advantage of the described process or method is the possibility of enabling a timely replacement of very likely problematic hoses, which ultimately leads to a higher availability of the devices and fewer repeated tests.

The current invention is based on evaluating the aspiration time related during a washing process which comprises an aspiration time basically of air and liquids. The method is described with reference to FIG. 1. The data is collected by optical sensors built into the instrument. A wash curve is for instance a sampled for measurement (110) of voltages from a photodiode that measures light intensities through a hose. During the aspiration process, the voltage of the photodiode is recorded at high frequency (120). The measured signals differ depending on whether the tube is filled with air or with liquid. This information can be used to detect air bubbles or, together with the knowledge of the pump's flow rate and its operating time, the amount of pumped liquid can also be determined. This information is used locally on the unit to detect faults in the process.

In addition, the recorded wash curves are then sent from the instrument to a cloud and stored. Based on said data, the actual suction time of the liquid from the voltage measurements is determined, among other things (130).

Two parameters, the aspiration time and information for the completeness of the wash curve (140) or aspiration process, are extracted from the curve and form the basis for the second processing step. Both parameters are evaluated using a sliding window approach over the most recent 40 consecutive wash curves to determine any changes and trends (150). If the changes of individual parameters in a sliding window of the last 30 measurements are too large, an indicator is set for this parameter, which can point to problems with a hose. These indicators are monitored by the model for each parameter over the period of the last 300 measurements.

A threshold may be set for both sets of data relating to the aspiration time and the determination whether the aspiration process was completed or not. The evaluation of the two sets of data may comprise the determination whether a set threshold is exceeded or not reached, depending on whether it is critical to stay below a threshold or above a threshold.

If one of these indicators consistently points to problems during the last 300 measurements, the hose in question is marked to be in a "warning" state. This state has no predefined end. Therefore, it can only be ended by a hose replacement or a transition to a state with a worse hose rating, hereafter called a "critical" state. The "critical" state is reached if the indicator of the second surveyed parameter also points to problems. After reaching the "critical" state, the hose is classified to be in the "imminent failure" state after a short time. In this state, a prediction of the "Remaining Useful Lifetime (RUL)" in days is made by the model. The RUL in days is determined based on the average use of the instrument per day. Therefore, the determined RUL in the "imminent failure" state is in a range between a few days to several weeks. As soon as the determined RUL reaches the value 0 days, the hose is transferred to the "total failure" state. The hose should already have been replaced here, as it leads to more measurement repetitions and ultimately to instrument failure.

All states can only be changed back to "normal" by changing the hoses. The detection of the hose change is also done via a method, i.e., via the evaluation of the sensor data. Afterwards, the evaluation of the hoses starts again with the approach as described above.

The results of the determination are presented with the help of a specific predictive maintenance dashboard. There, the current condition of the hoses and the RUL are displayed. In addition, the determined parameters are displayed over time, so that a manual check of the predictions can be carried out, if necessary.

The availability of the units can be optimised by a timely replacement of the hoses or tubes marked as being "problematic". It also reduces the number of repetitions of unsuccessful tests, which also increases the instrument throughput. In addition, it is conceivable to soften the set replacement intervals for the instruments if no problems with the tubing are identified by the model.

Various alternative approaches for monitoring the hoses are conceivable. A more impractical solution would be to manually inspect the hoses on a weekly basis. This would allow for the detection of any obvious defects. However, this approach is very expensive, time consuming and requires trained personnel.

As an alternative to monitoring suction times of the bubble sensors used for the determination of a hoses' current state, it would also be conceivable to check the state of a hose using data from the peristaltic pump. For example, the current required for rotation could be measured to indicate the hoses' condition. Another alternative to the bubble sensor would be to determine the flow rate with the help of flow sensors built into the hose or tube.

Furthermore, it is also easily possible to choose other lengths for the sliding windows described above.

Finally, instead of a fixed starting value, a regression with the help of additional process data can be used for the prediction of the RUL. It is planned to use regression for the prediction of the RUL in the future.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for determining the quality of a hose in a peristaltic pump of an automated analyser system, comprising the steps of collecting data of an aspiration process through the hose by
  i. measuring the light intensity through the hose during aspiration with an optical sensor;
  ii. determining and recording the voltage changes related to changing light intensities measured by the optical sensor;

extracting an aspiration time and determining whether the aspiration process was completed from two sets of data of voltage changes relating to the aspiration time and whether the aspiration process was completed;

determining changes in the two sets of data of voltage changes for the aspiration time and the determination whether the process was completed;

setting a threshold for each set of data of voltage changes for the aspiration time and the time for determining whether the aspiration process was completed for indicating wear of the hose when at least one of the thresholds is exceeded or not reached, respectively;

replacement of the hose based on the wear indication.

2. The method of claim 1, wherein the state of the hose is classified as normal if none of both thresholds is exceeded or not reached, respectively.

3. The method of claim 2, wherein the state of the hose is set to 'warning' if at least one threshold is exceeded or not reached, respectively.

4. The method of claim 3, wherein the state of the hose is set to 'critical' if both thresholds are exceeded or not reached, respectively.

5. The method of claim 4, wherein the remaining useful lifetime of the hose is determined in days based on the average use of the automated analyser system per day.

6. The method of claim 5, wherein the state of the hose is set to 'total failure' when the last day of the determined days of the remaining useful lifetime has been reached.

7. The method of claim 3, wherein the state of the hose is set back to 'normal' following its replacement and the detection that none of both thresholds is exceeded or not reached, respectively.

8. The method of claim 4, wherein the state of the hose is set back to 'normal' following its replacement and the detection that none of both thresholds is exceeded or not reached, respectively.

9. The method of claim 5, wherein the state of the hose is set back to 'normal' following its replacement and the detection that none of both thresholds is exceeded or not reached, respectively.

10. The method of claim 6, wherein the state of the hose is set back to 'normal' following its replacement and the detection that none of both thresholds is exceeded or not reached, respectively.

11. The method of claim 1, wherein the recent 40 wash curves are used for determining changes in the two sets of data of voltage changes for the aspiration time and for determining whether the aspiration process was completed.

12. The method of claim 1, wherein the recording of voltages of a light barrier's photodiode is done at high frequencies during a washing process.

* * * * *